(12) United States Patent
Kim et al.

(10) Patent No.: US 9,801,943 B2
(45) Date of Patent: Oct. 31, 2017

(54) METHOD FOR IN VIVO TARGETING OF NANOPARTICLES VIA BIOORTHOGONAL COPPER-FREE CLICK CHEMISTRY

(71) Applicant: KOREA INSTITUTE OF SCIENCE AND TECHNOLOGY, Seoul (KR)

(72) Inventors: Kwang Meyung Kim, Seoul (KR); Ick Chan Kwon, Seoul (KR); Kuiwon Choi, Seoul (KR); Heebeom Koo, Seoul (KR); Sang-min Lee, Seoul (KR); Inchan Youn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 449 days.

(21) Appl. No.: 13/774,247

(22) Filed: Feb. 22, 2013

(65) Prior Publication Data

US 2013/0251784 A1    Sep. 26, 2013

(30) Foreign Application Priority Data

Mar. 20, 2012   (KR) .................... 10-2012-0028370

(51) Int. Cl.
*A61K 47/26* (2006.01)
*A61K 47/34* (2017.01)
(Continued)

(52) U.S. Cl.
CPC .............. *A61K 47/26* (2013.01); *A61K 47/34* (2013.01); *A61K 47/4813* (2013.01);
(Continued)

(58) Field of Classification Search
None
See application file for complete search history.

(56) References Cited

U.S. PATENT DOCUMENTS

2008/0248126 A1* 10/2008 Cheng ................. A61K 47/482
                                                                           514/1.1
2009/0074674 A1*  3/2009 Katti ..................... A61K 9/148
                                                                           424/9.42

FOREIGN PATENT DOCUMENTS

WO    WO-2012-075361    * 7/2012

OTHER PUBLICATIONS

Koo H, Bioorthogonal copper-free click chemistry in vivo tumor-targeted delivery of nanoparticles, agnew chem int ed, 2012, 51, 11836-11840.*

(Continued)

*Primary Examiner* — Celeste A Roney
(74) *Attorney, Agent, or Firm* — Goldilocks Zone IP Law

(57) ABSTRACT

The present disclosure relates to a method for in vivo targeting of a nanoparticle via bioorthogonal copper-free click chemistry, more particularly to a method for in vivo targeting of a nanoparticle, including: injecting a precursor capable of being metabolically engineered in vivo when injected into a living system and having a first bioorthogonal functional group into the living system; and injecting a nanoparticle having a second bioorthogonal functional group which can perform a bioorthogonal copper-free click reaction with the first bioorthogonal functional group attached thereto into the living system.
In accordance with the present disclosure, accumulation of nanoparticles at a target site in a living system can be increased remarkably and the biodistribution of the nanoparticles can be controlled since the nanoparticles bound to a cell surface are taken up into the cell with time.

4 Claims, 9 Drawing Sheets

(51) Int. Cl.
*A61K 47/48* (2006.01)
*A61K 49/00* (2006.01)

(52) U.S. Cl.
CPC .. *A61K 47/48092* (2013.01); *A61K 47/48815* (2013.01); *A61K 49/0032* (2013.01); *A61K 49/0052* (2013.01)

(56) References Cited

OTHER PUBLICATIONS

Agard N, A strain promoted [3+2] azide-alkyne cycloaddition for covalent modification of biomolecules in living systems, JACS, 2004, 126, 15046-15047.*
Von Maltzhan G, In vivo tumor cell targeting with click nanoparticles, Bioconjugate Chem, 2008, 19, 1570-1578.*
Chang PV, Copper free click chemistry in living animals, PNAS, Feb. 2, 2010, 107, 5, 1821-1826.*

\* cited by examiner

METHOD FOR IN VIVO TARGETING OF NANOPARTICLES VIA BIOORTHOGONAL COPPER-FREE CLICK CHEMISTRY

CROSS-REFERENCE TO RELATED APPLICATIONS

This application claims priority under 35 U.S.C. §119 to Korean Patent Application No. 10-2012-0028370 filed on Mar. 20, 2012, in the Korean Intellectual Property Office, the disclosure of which is incorporated herein by reference in its entirety.

TECHNICAL FIELD

The present disclosure relates to a method for delivering nanoparticle to a target tissue in vivo via bioorthogonal copper-free click chemistry.

BACKGROUND

The concept of bioorthogonal chemistry is summarized by Carolyn Bertozzi et al. in 2003 (Sletten, Ellen M.; Bertozzi, Carolyn R. "From Mechanism to Mouse: A Tale of Two Bioorthogonal Reactions" Acc. Chem. Res., 2011, 44 (9), pp 666-676). It refers to any chemical reaction that can occur inside of living systems without interfering with native biochemical processes. Some bioorthogonal compounds react only with specific unnatural molecules injected from outside, without reacting with biomolecules in the living system. The use of bioorthogonal chemistry typically proceeds in two steps as follows. First, a cellular substrate is modified with a bioorthogonal functional group and introduced into a cell. The cellular substrate may be a metabolite, an enzyme inhibitor, etc. The bioorthogonal functional group must not alter the structure of the substrate dramatically to avoid affecting its bioactivity. Secondly, a probe having a complementary functional group reacting with the bioorthogonal functional group is introduced to react with and label the substrate.

Recently, the bioorthogonal chemistry is paving the way for many novel innovations in the biological field. Direct chemical reactions applicable in living systems with both bioorthogonality and biocompatibility have garnered much attention from both chemists and biologists. For example, although the Staudinger ligation of azides with phosphines represented by Scheme 1 exhibits bioorthogonality under both in vitro and in vivo conditions, its wide application is restricted due to slow reaction kinetics.

<Scheme 1>

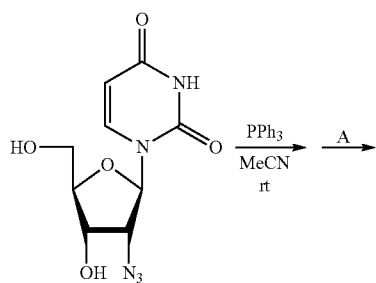

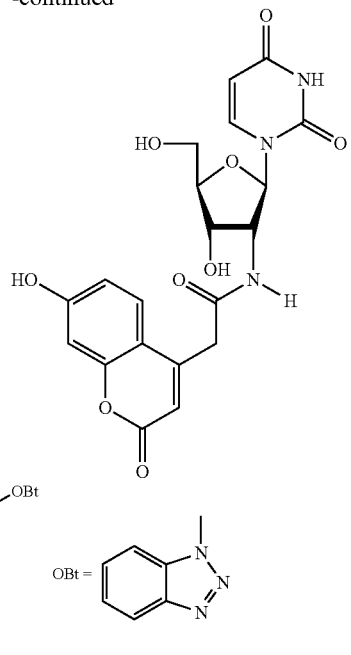

Bertozzi et al. have developed many chemicals for biocompatible copper-free click chemistry by focusing on ring-strained alkyne groups as the counterparts to azide groups for increased reactivity. Weissleder et al. have also developed a tetrazine cycloaddition reaction which is extremely fast and highly specific.

In particular, the reason why copper-free click chemistry is required is because, although the classic azide-alkyne cycloaddition using a copper catalyst is a very fast and effective reaction for bioconjugation, it is not suitable for use in live cells due to the toxicity of Cu(I) ions.

As shown in FIG. 5, Bertozzi et al. have developed a bioorthogonal copper-free click chemical reaction requiring no copper catalyst. The reaction is a strain-promoted alkyne-azide cycloaddition.

The potentiality of bioorthogonal chemistry has been proven in many applications. In particular, bioorthogonal chemistry has shown powerful applications in biological fields in combination with metabolic glycoengineering. Through metabolic glycoengineering, unnatural glycans are introduced into cells by feeding specific precursors on the basis of their intrinsic metabolism. Bertozzi's group has pioneered this special technique and demonstrated that modified functional groups can be introduced for bioorthogonal chemistry using the technique. Specifically, the technique has been excellently applied for various purposes, including analysis of cellular glycans, 3D cellular assembly, exploration of metabolic pathways and spatiotemporal imaging of zebrafish development. However, there are few reports on in vivo studies of vertebrates and researches in this field are less active than those in cellular level.

Meanwhile, nanoparticles have emerged as a promising tool in the biomedical field, in which they serve as delivery carriers of imaging agents or nanodrugs. Active targeting is the typical method of improving the specificity of the nanoparticles to disease sites. For active targeting, biological targeting moieties such as antibodies, aptamers or peptides capable of binding to proper receptors on the surface of target cells are used. However, since the number of the receptors binding to the materials is limited, the capacity of the targeting nanoparticles is limited when the receptors are saturated. In addition, because targetable receptors are rarely unique to the disease, the nanoparticles may accumulate in other healthy tissues through these receptors, resulting in reduced therapeutic efficacy or unintended side effects.

SUMMARY

The present disclosure is directed to providing a novel method for in vivo targeting of nanoparticles based on bioorthogonal copper-free click chemistry, allowing remarkably increased accumulation of the nanoparticles at the target site and control of the in vivo distribution of the nanoparticles as the nanoparticles are taken up into cells with time.

In one general aspect, there is provided a method for in vivo targeting of a nanoparticle, including:

injecting a precursor capable of being metabolically engineered in vivo when injected into a living system and having a first bioorthogonal functional group into the living system; and injecting a nanoparticle having a second bioorthogonal functional group which can perform a bioorthogonal copper-free click reaction with the first bioorthogonal functional group attached thereto into the living system.

In an exemplary embodiment of the present disclosure, the metabolic engineering may be metabolic glycoengineering.

In another exemplary embodiment of the present disclosure, the precursor may be a compound selected from a group consisting of Chemical Formulas 1 to 3:

<Chemical Formula 1>

<Chemical Formula 2>

<Chemical Formula 3>

In another exemplary embodiment of the present disclosure, the first bioorthogonal functional group may be an azide group.

In another exemplary embodiment of the present disclosure, the second bioorthogonal functional group may be a functional group capable of reacting with the first bioorthogonal functional group in vivo in the absence of a catalyst.

In another exemplary embodiment of the present disclosure, the second bioorthogonal functional group may be a compound selected from a group consisting of Chemical Formulas 4 to 15:

<Chemical Formula 4>

<Chemical Formula 5>

<Chemical Formula 6>

<Chemical Formula 7>

<Chemical Formula 8>

<Chemical Formula 9>

<Chemical Formula 10>

<Chemical Formula 11>
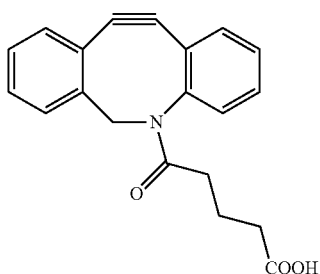

<Chemical Formula 12>
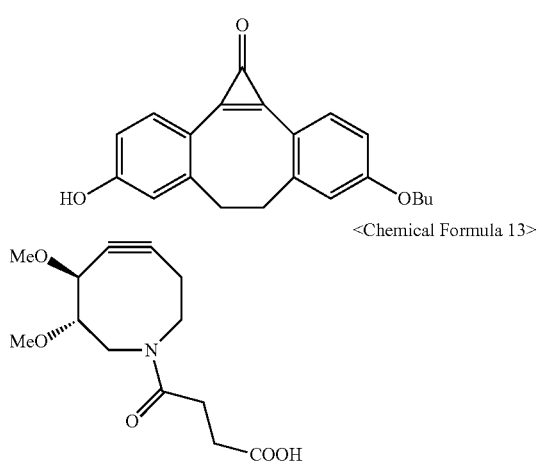

<Chemical Formula 13>

<Chemical Formula 14>
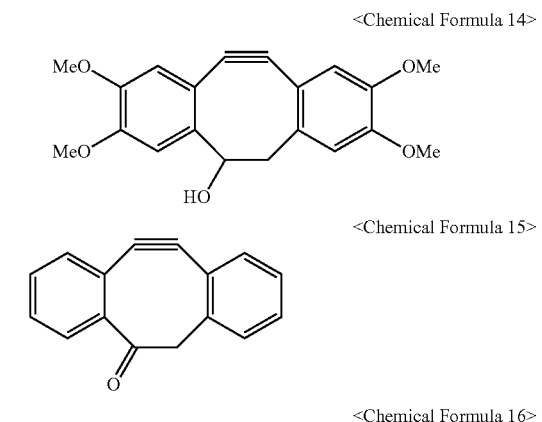

<Chemical Formula 15>

<Chemical Formula 16>
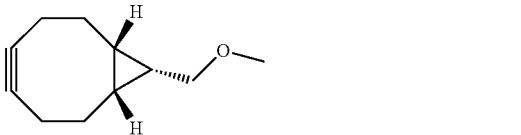

In another exemplary embodiment of the present disclosure, the nanoparticle may have a surface to which the second bioorthogonal functional group can be attached and may have a size of 10-1000 nm such that in vivo circulation is possible.

In another exemplary embodiment of the present disclosure, the nanoparticle may be an organic nanoparticle, an inorganic nanoparticle or an organic-inorganic hybrid nanoparticle.

In another exemplary embodiment of the present disclosure, the organic nanoparticle may be selected from a group consisting of liposome, micelle, polymer carrier and protein nanoparticles and the inorganic nanoparticle may be selected from a group consisting of iron oxide, gold and silica nanoparticles.

BRIEF DESCRIPTION OF THE DRAWINGS

The above and other objects, features and advantages of the present disclosure will become apparent from the following description of certain exemplary embodiments given in conjunction with the accompanying drawings, in which.

DETAILED DESCRIPTION OF EMBODIMENTS

Figure 1:
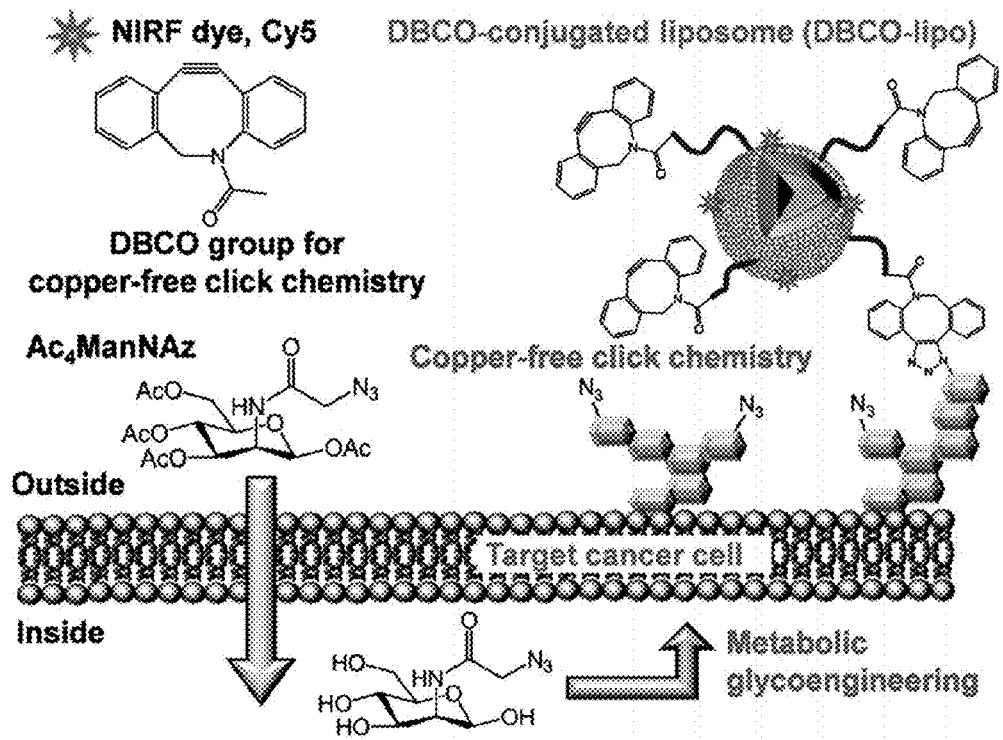
FIG. 1 schematically illustrates a method for in vivo targeting of a nanoparticle by bioorthogonal copper-free click chemistry according to an exemplary embodiment of the present disclosure.

Hereinafter, exemplary embodiments will be described in detail with reference to the accompanying drawings.

The present disclosure is directed to providing a method for in vivo targeting of a nanoparticle via bioorthogonal copper-free click chemistry. Specifically, it presents the possibility of generating a functional group modified by metabolic engineering at the target site in a living system. The modified functional group may be used as a means for delivering a nanoparticle to the target in vivo by bioorthogonal copper-free click chemistry. In accordance with the present disclosure, dose-dependent and temporal generation of a chemical functional group is possible on the target disease site and in vivo distribution of nanoparticles can be controlled just like biological receptors. Furthermore, the bioorthogonal chemistry employed in the present disclosure can be more effectively applied to nanoparticles than other small molecules, because the multivalent effect and the longer circulation time of nanoparticles provide more chances of binding to the cell surface. As described in the Examples section, the inventors of the present disclosure investigated the intracellular fate of the nanoparticles chemically bound to the cell surface, which is important for their application as drug carriers.

Specifically, a method for in vivo targeting of a nanoparticle according to the present disclosure comprises: injecting a precursor capable of being metabolically engineered in vivo when injected into a living system and having a first bioorthogonal functional group into the living system; and injecting a nanoparticle having a second bioorthogonal functional group which can perform a bioorthogonal copper-free click reaction with the first bioorthogonal functional group attached thereto into the living system.

The precursor may be selected from a group consisting of tetraacetylated N-azidoacetyl-D-mannosamine (Chemical Formula 1), tetraacetylated N-azidoacetyl-D-galactosamine (Chemical Formula 2) and tetraacetylated N-azidoacetyl-D-glucosamine (Chemical Formula 3), which are known as precursors for metabolic glycoengineering. Besides, any precursor capable of being introduced to a cellular substrate, a nucleic acid, a protein, etc. through metabolism may be used without limitation.

<Chemical Formula 1>

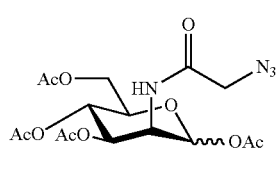

<Chemical Formula 2>

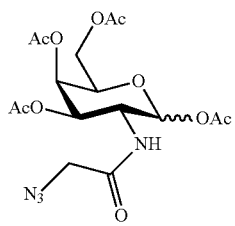

<Chemical Formula 3>

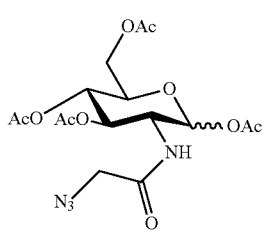

The first bioorthogonal functional group may be representatively an azide group ($N_3$). In addition, it may be any functional group if it is capable of reacting with the second bioorthogonal functional group in vivo in the absence of a catalyst. The second bioorthogonal functional group may be a functional group capable of reacting with the first bioorthogonal functional group in vivo in the absence of a catalyst, such as a dibenzylcyclootyne (DBCO) group or a ring-strained alkyne group. For example, the compounds of Chemical Formulas 4 to 15 may be used:

<Chemical Formula 4>

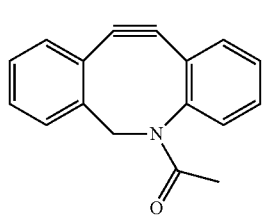

<Chemical Formula 5>

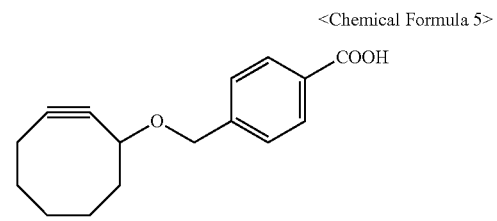

<Chemical Formula 6>

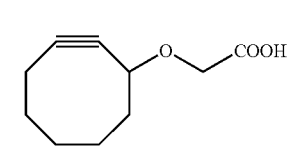

<Chemical Formula 7>

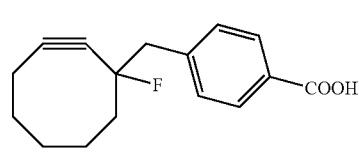

<Chemical Formula 8>

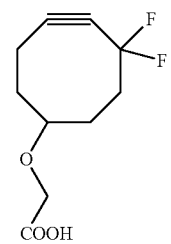

<Chemical Formula 9>

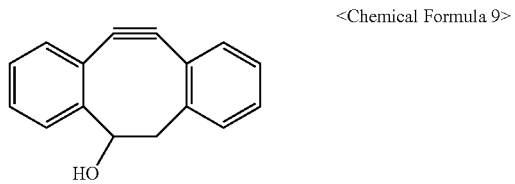

<Chemical Formula 10>

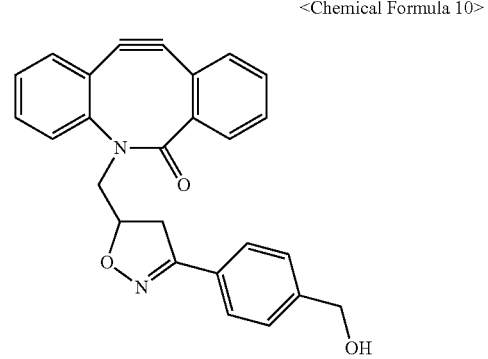

<Chemical Formula 11>
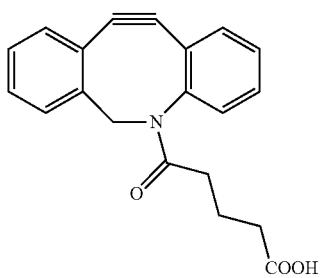

<Chemical Formula 12>
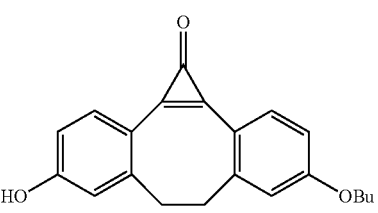

<Chemical Formula 13>
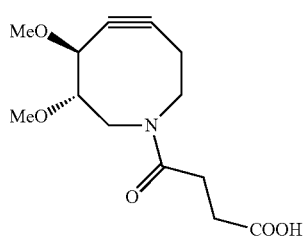

<Chemical Formula 14>
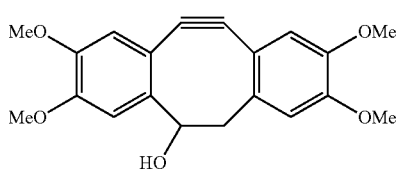

<Chemical Formula 15>
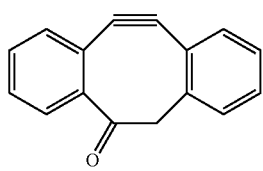

<Chemical Formula 16>
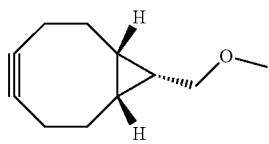

The nanoparticle is not particularly limited as long as it has a surface to which the second bioorthogonal functional group can be attached and has a size of 10-1000 nm such that in vivo circulation is possible. Specific examples may include organic nanoparticles such as liposome, micelle, polymer carrier and protein nanoparticles, inorganic nanoparticles such as of iron oxide, gold and silica nanoparticles, or organic-inorganic hybrid nanoparticles.

For example, FIG. 1 schematically illustrates a method for in vivo targeting of a nanoparticle by bioorthogonal copper-free click chemistry according to an exemplary embodiment of the present disclosure, wherein tetraacetylated N-azidoacetyl-D-mannosamine is used as the precursor having the first bioorthogonal functional group and a compound with a dibenzylcyclootyne group attached to amine-functionalized polyethylene glycol (PEG)-liposome is used as the nanoparticle having the second bioorthogonal functional group attached thereto. Referring to FIG. 1, the tetraacetylated N-azidoacetyl-D-mannosamine ($Ac_4ManNAz$) injected into the living system as the precursor having the first bioorthogonal functional group forms an azide group attached to the cell membrane via metabolic glycoengineering in the cell. Then, when the substance with the dibenzylcyclootyne group attached to the amine-functionalized PEG-liposome is injected into the living system as the nanoparticle, copper-free click chemical reaction occurs between the azide group attached to the cell membrane and the dibenzylcyclootyne group. Accordingly, the PEG-liposome bound to the cell membrane does not remain fixed to the cell surface but is transported into the cell via the intrinsic glycan internalization process. Accordingly, the method according to the present disclosure can deliver a specific drug into the cell via the nanoparticle.

In an experiment where liposomes were labeled with the fluorescent dye Cy5.5 for effective tracking, the amount of DBCO-functionalized liposome (DBCO-lipo) bound on the cell surface increased along with the increasing number of azide groups, as will be described in the Examples section. This indicates the high reactivity of the copper-free click chemistry. The fluorescence intensity of DBCO-lipo was much higher than that of DBCO-SETA. This may be attributable to the multivalent effect of the nanoparticle since one fluorescent dye in the DBCO-lipo has about 20 DBCO groups.

EXAMPLES

Hereinafter, the present disclosure will be described in more detail through examples. However, the following examples and experiments are for illustrative purposes only and not intended to limit the scope of this disclosure.

Materials 1,2-Dipalmitoyl-sn-glycero-3-phosphocholine (DPPC), 1,2-dipalmitoyl-sn-glycero-3-phosphoethanolamine (DPPE), cholesterol (CHOL) and 1,2-distearoyl-sn-glycero-3-phosphoethanolamine-N-[amino(polyethylene glycol) 2000] (DSPE-PEG 2000-$NH_2$) were purchased from Avanti Polar Lipids (Alabaster, Ala., USA). Sulfo-dibenzylcyclooctyne-NHS ester (sulfo-DBCO-NHS) and dibenzylcyclooctyne-SETA650 (DBCO-dye conjugate) were purchased from Click Chemistry Tools (Scottsdale, Ariz., USA). Tetraacetylated N-azidoacetyl-D-mannosamine ($Ac_4ManNAz$) was purchased from Invitrogen (Carlsbad, Calif., USA). 4-(Dimethylamino)pyridine (DMAP), 4-methylmorpholine (NMM) and tris(2-carboxyethyl)phosphine (TCEP) were purchased from Sigma-Aldrich (St. Louis, Mo., USA). A monoreactive hydroxysuccinimide ester of Cy5.5 (Cy5.5-NHS) was purchased from Amersham Biosciences (Piscataway, N.J., USA). Methanol, chloroform and ether were purchased from Merck (Darmstadt, Germany). All the chemicals were of analytical grade and used without further purification.

Synthesis of DSPE-PEG 2000-DBCO

DSPE-PEG 2000-DBCO was synthesized by reacting 10 molar equivalents of sulfo-DBCO-NHS (22 mg, 35.7 μmol) with DSPE-PEG 2000-$NH_2$ (10 mg, 3.57 μmol) in 10 mL of a chloroform/methanol mixture (2:1, v/v) at room temperature for 6 hours. After the reaction, the solution was dialyzed against water and methanol using a cellulose membrane (MWCO 1000: Spectrum Laboratories, CA, USA) at room temperature to remove excess sulfo-DBCO-NHS, NMM and DMAP and then lyophilized to obtain DSPE-PEG 2000-

DBCO. $^1$H nuclear magnetic resonance ($^1$H NMR) spectra were obtained at 600 MHz using CDCl$_3$ as a solvent.

Synthesis of Cy5.5-Labeled DPPE

To label liposomes with Cy5.5 for fluorescence tracking, Cy5.5-labeled DPPE was synthesized by conjugating Cy5.5-NHS with DPPE using the same method as described above. Briefly, DPPE (3.5 mg, 5 μmol) dissolved in 3.5 mL of a chloroform/methanol mixture (2:1, v/v) was incubated with Cy55-NHS (6 mg, 10 μmol) at room temperature. The reaction was conducted overnight at room temperature in the dark. The obtained Cy5.5-labeled DPPE was crystallized in ether and dried for 3 days under vacuum.

Preparation and Characterization of DBCO-Lipo

Dried lipids were mixed in a chloroform/methanol mixture (2:1, v/v) in a glass vial with a composition of DPPC:CHOL:DSPE-PEG 2000-DBCO:DPPE-Cy5.5=54.5:35:10:0.5 (molar ratio). Control liposomes without DBCO contained DSPE-PEG 2000-NH$_2$ instead of DSPE-PEG 2000-DBCO. The organic solvent was evaporated using a rotary evaporator to obtain a thin lipid film deposited on the glass vial wall. The lipid film was freeze-dried overnight to remove traces of remaining organic solvent and then hydrated and dispersed in PBS (pH=7.4) by vortex mixing. The resulting multilamellar vesicles (MLVs) were kept at room temperature for 30 minutes and then sonicated at 90 W for 2 minutes using a probe-type sonicator (Ultrasonic Processor, Cole-Parmer Inst. Co.) to prepare nano-sized small unilamellar vesicles (SUVs). The resulting liposomes were kept at room temperature for 30 minutes and then passed through a syringe filter membrane (0.45 μm, cellulose acetate, Millipore). The morphology of the liposomes was observed by cryogenic transmission electron microscopy (cryo-TEM). Cryo-TEM images were obtained at about −170° C. using 200-kV Tecnai F20 (FEI, Netherlands). The average diameter and size distribution of the liposomes were determined using Zetasizer Nano ZS (Malvern Instruments, Worcestershire, UK).

Cell Culture

Human lung adenocarcinoma cells (A549) purchased from ATCC (Manassas, Va., USA) were cultured in RPMI-1640 (Welgene, Daegu, Korea) supplemented with 10% fetal bovine serum (FBS; Welgene, Daegu, Korea), 100 U/mL penicillin and 100 μg/mL streptomycin (Welgene, Daegu, Korea) at 37° C. under a humidified 5% CO$_2$ atmosphere.

Western Blot Analysis of Cells

A549 cells in 10 mL of media with no sugar or different concentrations of Ac$_4$ManNAz (final concentrations of 0.5 μM, 5 μM and 50 μM) were seeded onto 100×20 mm polystyrene tissue culture plates at a density of 1.5×10$^6$ cells per plate and incubated for 3 days. The cells were washed twice with PBS (pH 7.4) and harvested from the plates with a cell scraper. The cells were pelletized by centrifuging at 3,000×g for 5 minutes and the supernatant was discarded. The cell pellets were resuspended in 500 μL of lysis buffer (1% SDS, 100 mM Tris.HCl, pH 7.4) containing protease inhibitor (Complete, EDTA-free) and lysed at 4° C. using a probe-type sonicator. The sonicated lysates were incubated at 4° C. for 30 minutes to further solubilize proteins. Insoluble debris was removed by centrifuging at 3,000×g for 10 minutes. Total soluble protein concentration was determined by the bicinchroninic acid (BCA) protein assay (Pierce, Ill., USA) to be 5 mg/mL. 20 μL of the lysate (5 mg/mL protein) was incubated with 2 μL of phosphine-FLAG (5 mM in PBS, pH 7.4) (Sigma, St. Louis, Mo., USA) at 37° C. for 6 hours. SDS-PAGE loading buffer was added to each sample. Then, aliquots were loaded onto 10% SDS-PAGE after heating at 95° C. Proteins were transferred to Hybond P membrane (Amersham, St. Albans, UK) and the membrane was blocked with 5% bovine serum albumin (BSA) in TBST (50 mM Tris.HCl, 150 mM NaCl, 0.1% Tween 20, pH 7.4) overnight at 4° C. The membrane was washed 3 times with TBST and incubated with monoclonal anti-FLAG-HRP antibody (diluted to 1:2,000 in TBST) (Sigma, St. Louis, Mo., USA) for 1.5 hours. The membrane was washed 3 times with TBST and developed using the ECL Prime western blotting detection reagent (Amersham, St. Albans, UK).

Cell Imaging

A549 cells in 2 mL of media with no sugar or 50 μM Ac$_4$ManNAz (final concentration) were seeded onto 35-mm glass-bottomed dishes at a density of 2×10$^4$ cells per dish and incubated for 3 days. The cells were washed twice with PBS (pH 7.4) containing Ca$^{2+}$ and Mg$^{2+}$ and fixed with a formaldehyde-glutaraldehyde combined fixative for 15 minutes at room temperature. Then, the cells were rinsed with PBS (pH 7.4), blocked with 5% BSA in PBS (pH 7.4) for 30 minutes at room temperature, and incubated with phosphine-FLAG (200 μM, final concentration) (Sigma, St. Louis, Mo., USA) in PBS (pH 7.4) containing 5% BSA for 4 hours at 37° C. After the incubation, the cells were rinsed 3 times with PBS (pH 7.4) containing 0.5% Tween 20, rinsed twice with PBS (pH 7.4), and then incubated with FITC-conjugated M2 anti-FLAG antibody (diluted to 1:100 in PBS containing 5% BSA, pH 7.4) (Sigma, St. Louis, Mo., USA) for 60 minutes at room temperature. The cells were washed twice with PBS (pH 7.4) and then stained with DAPI (Invitrogen, Carlsbad, Calif.) to label the nuclei.

A549 cells in 2 mL of media with no sugar or different concentrations of Ac$_4$ManNAz (final concentrations of 0.5 μM, 5 μM and 50 μM) were seeded onto 35-mm glass-bottomed dishes at a density of 2×10$^4$ cells per dish and incubated for 3 days. Prior to the experiment, the cells were washed twice with PBS (pH 7.4) containing Ca$^{2+}$ and Mg$^{2+}$ and incubated for 2 hours in serum-free transfection media. After the incubation, the cells were washed twice with PBS (pH 7.4) containing Ca$^{2+}$ and Mg$^{2+}$, fixed using a formaldehyde-glutaraldehyde combined fixative for 15 minutes at room temperature, and then stained with DAPI (Invitrogen, Carlsbad, Calif.) to label the nuclei. For quenched controls, the cells were treated with 10 mM TCEP (PBS, pH 7.4) in serum-free transfection medium for 10 minutes and then incubated with DBCO-lipo (100 μg/mL) in 2 mL serum-free transfection medium at 37° C. for 30 minutes.

For time-lapse imaging, 2×10$^4$ A549 cells in 2 mL of medium containing 50 μM Ac$_4$ManNAz (final concentration) were seeded onto a 35-mm glass-bottomed dish and incubated for 3 days. Prior to the experiment, the cells were washed twice with PBS (pH 7.4) containing Ca$^{2+}$ and Mg$^{2+}$ and incubated in serum-free medium for 2 hours. The A549 cells were further incubated with DBCO-lipo (100 μg/mL) in 2 mL of serum-free transfection medium at 37° C. for 1 hour. The cells were washed twice with PBS (pH 7.4) containing Ca$^{2+}$ and Mg$^{2+}$ and the medium was replaced with a fresh growth medium. The cells were fixed at different time points from 10 minutes to 24 hours.

All cellular images were obtained using the FluoView FV1000 confocal laser scanning microscope (Olympus, Tokyo, Japan) equipped with 405 diode (405 nm) and HeNe-Red (633 nm) lasers.

Flow Cytometry Analysis

A549 cells in 2 mL of media with no sugar or different concentrations of Ac$_4$ManNAz (final concentrations of 0.5 μM, 5 μM and 50 μM) were seeded onto a 6-well plate at a density of 2×10$^4$ cells per well and incubated for 3 days.

Prior to the experiment, the cells were washed twice with PBS (pH 7.4) containing $Ca^{2+}$ and $Mg^{2+}$ and incubated in serum-free transfection media for 2 hours. The A549 cells were incubated with DBCO-lipo, control liposome at a concentration of 100 μg/mL without containing DBCO, or DBCO-fluorescent dye conjugate having the same fluorescence intensity as DBCO-lipo at 37° C. for 1 hour in 2 mL of serum-free transfection media. After the incubation, the cells were lifted by incubating at 37° C. in PBS (pH 7.4) containing 1 mM EDTA and 1% FBS (FACS buffer) and washed twice with FACS buffer. 50,000 cells were analyzed per sample by flow cytometry (BD FACSCalibur, BD Biosciences, San Jose, Calif., USA) and the obtained data were analyzed using the FlowJo software.

In Vivo and Ex Vivo NIRF Imaging

All experiments using live animals were performed in compliance with the relevant laws and the institutional guidelines of the Korea Institute of Science and Technology (KIST) and under the approval by the institutional committee. For in vivo and ex vivo experiments, $1.0 \times 10^7$ A549 tumor cells were administered to 5-week-old male athymic nude mice (20 g, Institute of Medical Science, Tokyo, Japan) on both flanks by subcutaneous injection. When the tumors grew to a size of about 100 $mm^2$, 20 μL of different concentrations of Ac4ManNAz (0.5 mM, 5 mM and 50 mM) were administered into the left tumors once daily for 3 days by intratumoral injection, while the same volume of saline was injected into the right tumors (n=5 per each). DBCO-lipo (10 mg/kg), DBCO-free control liposome (10 mg/kg) or DBCO-fluorescent dye conjugate of the same fluorescence intensity as DBCO-lipo were injected into the tail veins of two A549 tumor-bearing mice. Their biodistribution and time-dependent tumor accumulation profile were non-invasively imaged using the eXplore Optix system (ART Advanced Research Technologies Inc., Montreal, Canada). Laser power and count time settings were optimized at 13 μW and 0.3 second per point. Excitation and emission spots were raster-scanned with 1 mm steps over the selected region of interest to generate emission wavelength scans. A 670-nm pulsed laser diode was used to excite Cy5.5 molecules. Near-infrared (NIR) fluorescence emission at 700 nm was collected and detected with a fast photomultiplier tube (Hamamatsu, Japan) and a time-correlated single photon counting system (Becker and Hickl GmbH, Berlin, Germany). The active tumor targeting characteristics of DBCO-lipo were evaluated by capturing 20 z-section images at 1.0 mm spacing using the Analysis Workstation software (ART Advanced Research Technologies Inc., Montreal, Canada). For quenched control, 20 μL of a TCEP solution (10 mM) was injected into the left tumor by intratumoral injection 1 hour before injection of DBCO-lipo. Major organs and tumors were dissected from the mice 5 hours after the injection of DBCO-lipo. NIR fluorescence images were obtained using a 12-bit CCD (Kodak Image Station 4000 MM, New Haven, Conn., USA) equipped with a Cy5.5 emission filter (600-700 nm; Omega Optical). The ex vivo NIR fluorescence images were quantified by measuring NIR fluorescence signal intensities at the regions of interest using the KODAK molecular imaging software. All numerical values were expressed as mean±standard deviation for the three animal groups.

Histological Analysis

The dissected tumor tissues were fixed in a 4% (v/v) buffered formalin solution, frozen in an optimum cutting temperature (OCT) compound (Sakura, Tokyo, Japan) on dry ice, and stored at −80° C. until use. Sections were cut on a cryostat (6 μm in thickness), picked up on slides containing poly-D-lysine, dried at 45° C., and then protected from light. Fluorescence was measured using the IX81-ZDC focus drift compensating microscope (Olympus, Tokyo, Japan) (excitation: 673 nm, emission: 692 nm).

Western Blot Analysis of Tumor Tissues

Preparation of tumor-bearing mouse models and administration of Ac4ManNAz were performed according to the same method as described above. 24 hours after the injection of Ac4ManNAz (on day 4), the tumors were dissected, transferred into 1 mL of lysis buffer (1% SDS, 100 mM Tris.HCl, pH 7.4) containing protease inhibitor (Complete, EDTA-free), and homogenized using a homogenizer (Wise-Mix HG-15D, Daihan Scientific, Seoul, Korea). The lysate was incubated at 4° C. for 30 minutes and insoluble debris was removed by centrifuging at 3,000×g for 10 minutes. Protein concentration was measured using the BCA protein assay kit. Staudinger reaction with phosphine-FLAG, SDS-PAGE and western blot analysis were conducted as described above.

Immunohistochemical Analysis

The dissected tumor tissues were retrieved and fixed in a 4% (v/v) buffered formalin solution, dehydrated with graded ethanol series, and embedded in paraffin. The paraffin tissues were sliced into 4-μm wide slices and immunohistochemical staining was performed using Histostain®-Plus Brod Spectrum (Invitrogen, CA, USA) in combination with phosphine-FLAG and monoclonal anti-FLAG-HRP antibodies according to the manufacturer's instructions. The paraffin slices were dehydrated, mounted using the Permount SP15-100 Toluene Solution (Fisher Scientific, NJ, USA) mounting medium, and observed with an optical microscope (BX51, Olympus, Tokyo, Japan). Images were photographed on a digital camera photomicroscope (DP71, Olympus, Tokyo, Japan).

Evaluation

Figure 2A:
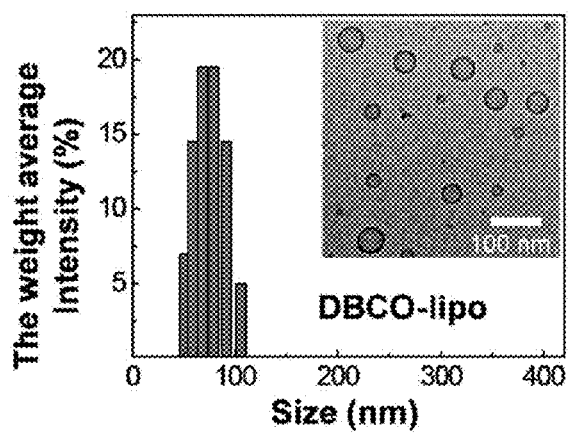
FIGS. 2a-2e show preparation of DBCO-functionalized liposome (DBCO-lipo) and binding to cells (FIG. 2a shows morphology (insert) and size distribution of DBCO-lipo, FIG. 2b shows a result of Coomassie staining and western blot analysis of Ac$_4$ManNAz-treated cells, FIG. 2c shows fluorescence intensity of Ac$_4$ManNAz-treated cells, FIG. 2d shows binding of DBCO-lipo to Ac$_4$ManNAz-treated cells, and FIG. 2e shows time-lapse images of Ac$_4$ManNAz-treated cells after binding with DBCO-lipo)

In the example described above, tetraacetylated N-azido-acetyl-D-mannosamine ($Ac_4ManNAz$) was selected for metabolic engineering of sialic acids localized primarily on the cell surface and dibenzylcyclootyne (DBCO) was chosen as a bioorthogonal chemical group because of its higher reactivity to azide groups through copper-free click chemistry in Staudinger reaction than phosphine. Activated DBCO (sulfo-DBCO-NHS) was conjugated to amine-functionalized PEG-liposomes and incorporated into liposomes during their fabrication by a traditional film casting method. For effective tracking, the liposomes were labeled with the fluorescent dye Cy5.5. The resulting liposomes had a stable spherical shape and a size of 75.33±18.29 nm as seen from CryoTEM images and DLS data (see FIG. 2a).

Figure 2B:
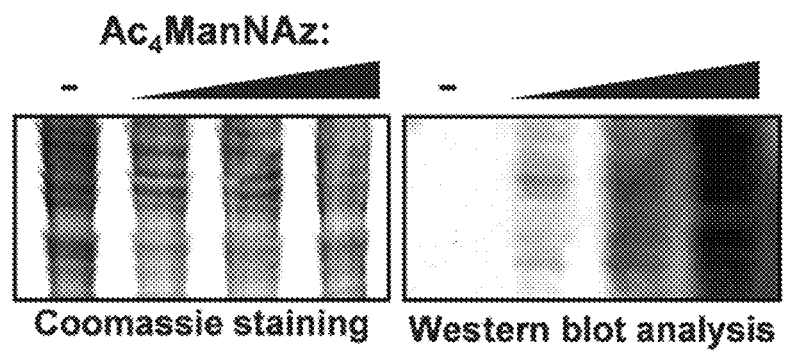
Figure 2C:
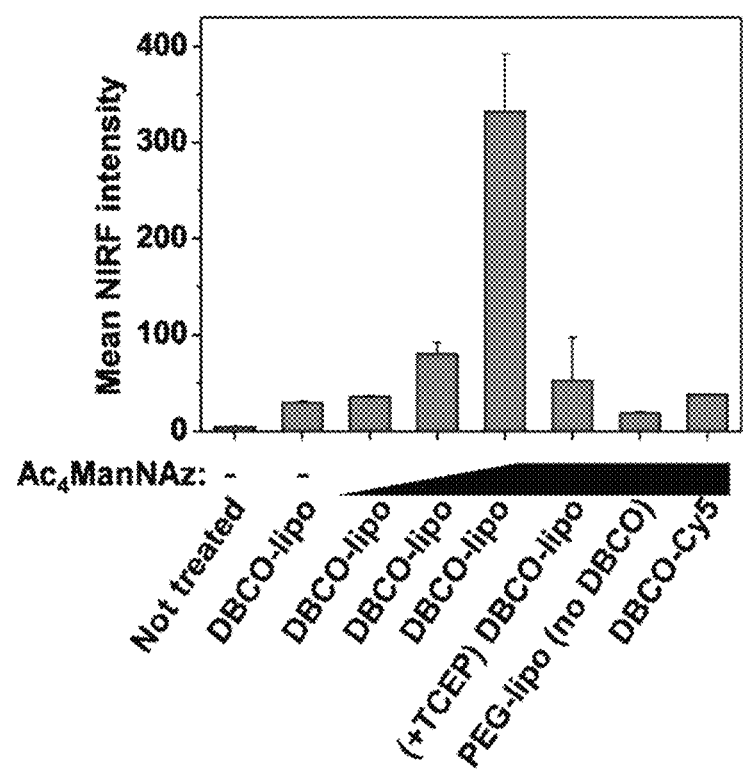

Generation of azide groups, binding with nanoparticles and cellular uptake thereof were tested in A549 human lung cancer cells. After administration of $Ac_4ManNAz$, modified azide groups could be generated on the surface of the A549 cells through metabolic glycoengineering. The correlation between the concentrations of the introduced azide groups and that of $Ac_4ManNAz$ in the cell culture medium could be inferred from Coomassie blue staining and western blot analysis of the cells (see FIG. 2b). When the cells were treated with DBCO-functionalized liposomes (DBCO-lipo), the amount of DBCO-lipo bound to the cell surface increased along with the increasing number of azide groups. This indicates the high reactivity of copper-free click chemistry. Interestingly, the fluorescence intensity was much higher than that of the DBCO-dye conjugate (DBCO-SETA). This may be attributable to the multivalent effect of the nanoparticles since one fluorescent dye in the DBCO-lipo has about 20 DBCO groups.

Figure 2D:
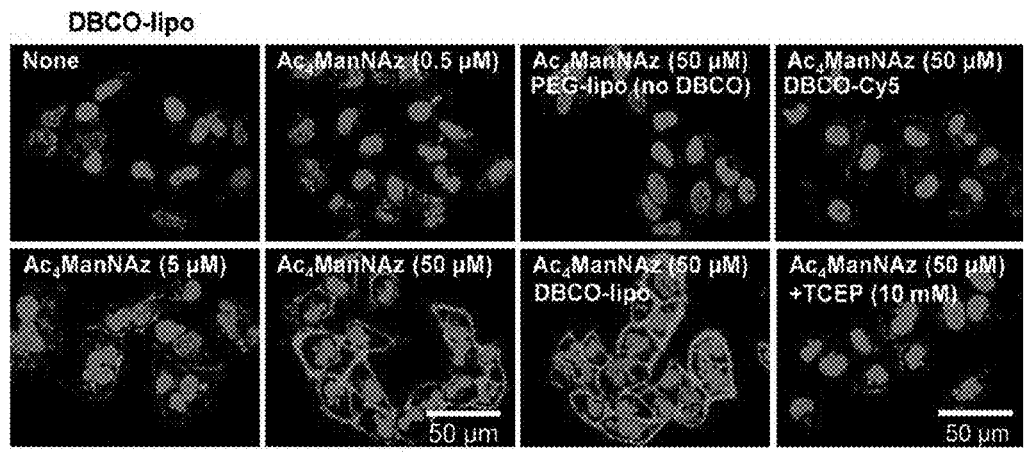
Figure 2E:
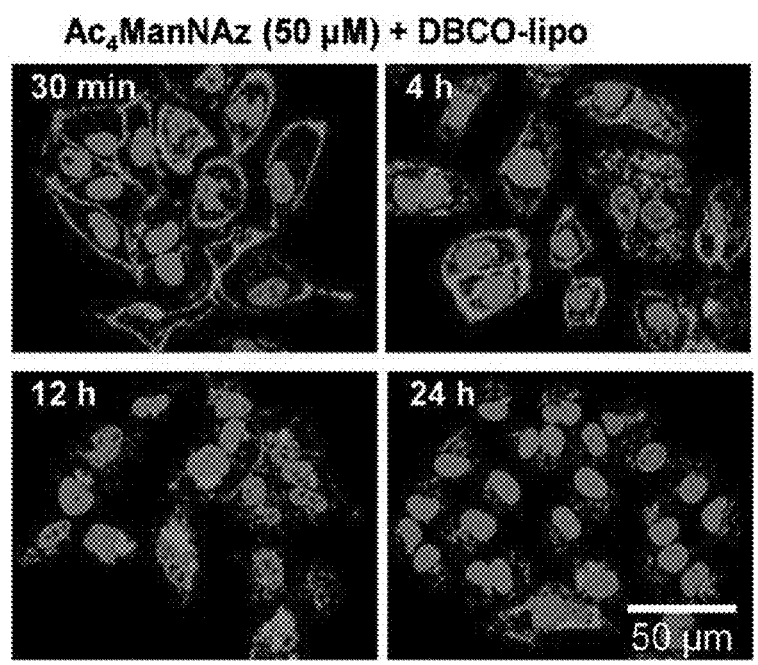

The fluorescence intensity of the cells treated with 50 μM Ac$_4$ManNAz was about 20-fold higher than that of the control cells not treated with Ac$_4$ManNAz, indicating that the binding of the liposomes was greatly enhanced. The azide groups on the cell surface can be greatly decreased with tris(2-carboxyethyl)phosphine (TCEP) under reducing condition. When the cells were pretreated with TCEP, the amount of the liposomes decreased drastically. This shows that the enhanced binding between DBCO and the azide group results from the chemical reaction. Importantly, the bound liposomes were taken up by the cells without remaining on the cell surface, as shown in the time-lapse images. It may be due to the intrinsic glycan internalization followed by endocytosis of the nanoparticles, which is significant for the intracellular delivery of drugs (see FIG. 2d).

Figure 3A:
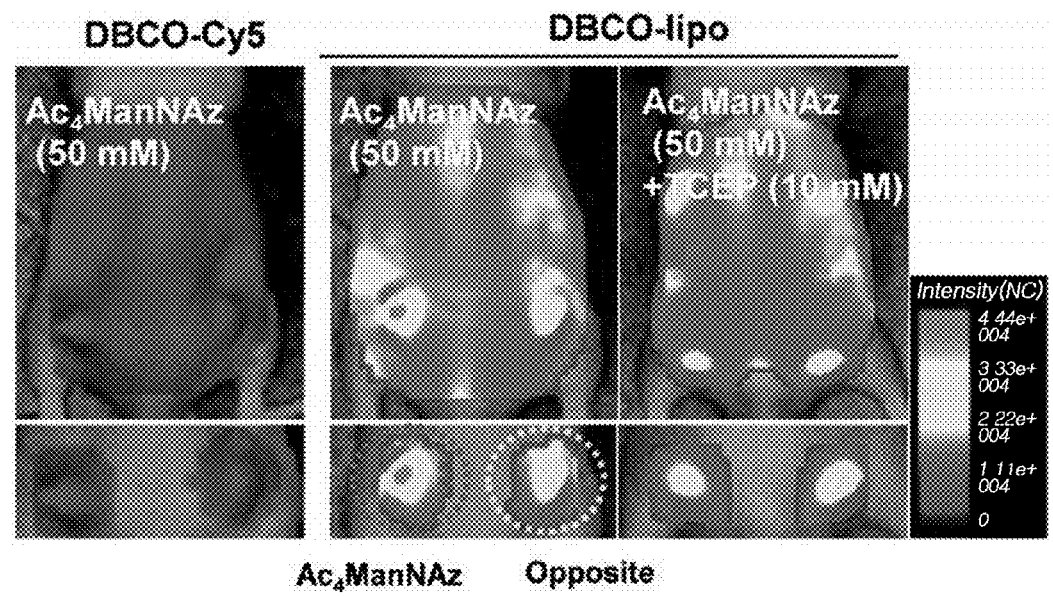
FIGS. 3a-3d show in vivo tumor targeting of DBCO-lipo in a tumor-bearing mouse model (FIG. 3a shows whole-body biodistribution of DBCO-lipo in a Ac$_4$ManNAz-treated tumor-bearing mouse, FIG. 3b shows z-section images of 50 mM Ac$_4$ManNAz-treated tumors after intravenous injection of DBCO-lipo, FIG. 3c shows ex vivo fluorescence images and fluorescence intensity of tumors in an Ac$_4$ManNAz-treated tumor-bearing mouse after intravenous injection of DBCO-lipo, and FIG. 3d shows ex vivo fluorescence images and fluorescence intensity of organs of a 50 mM Ac$_4$ManNAz-treated mouse after intravenous injection of DBCO-lipo)
Figure 3B:
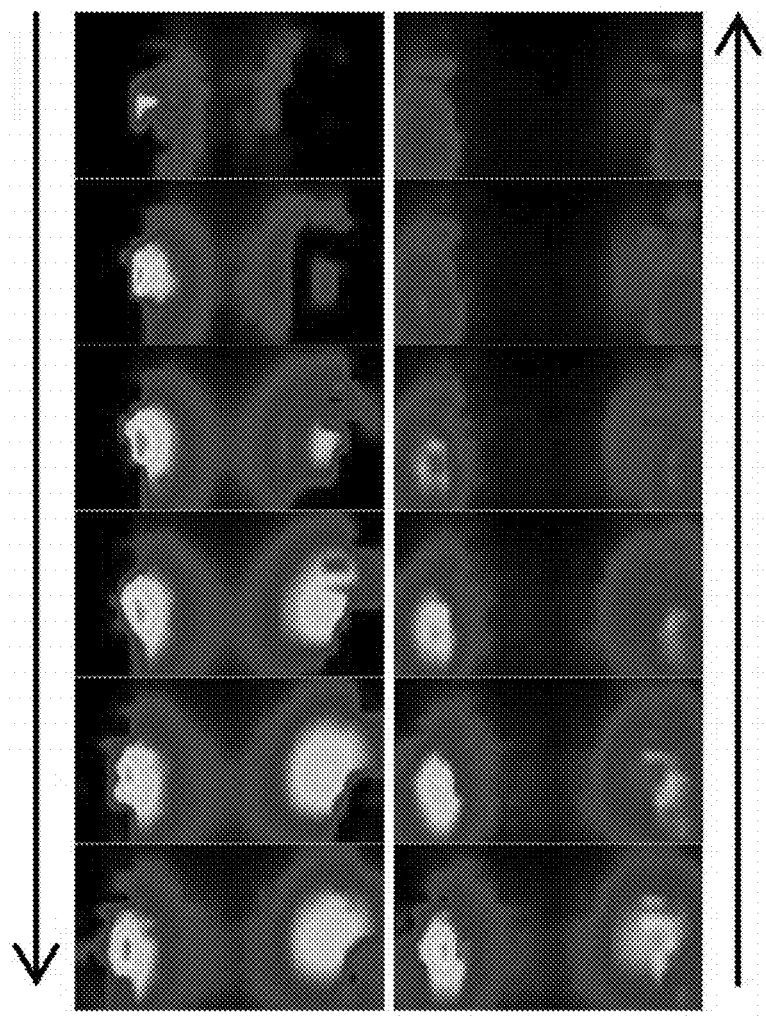
Figure 3C:
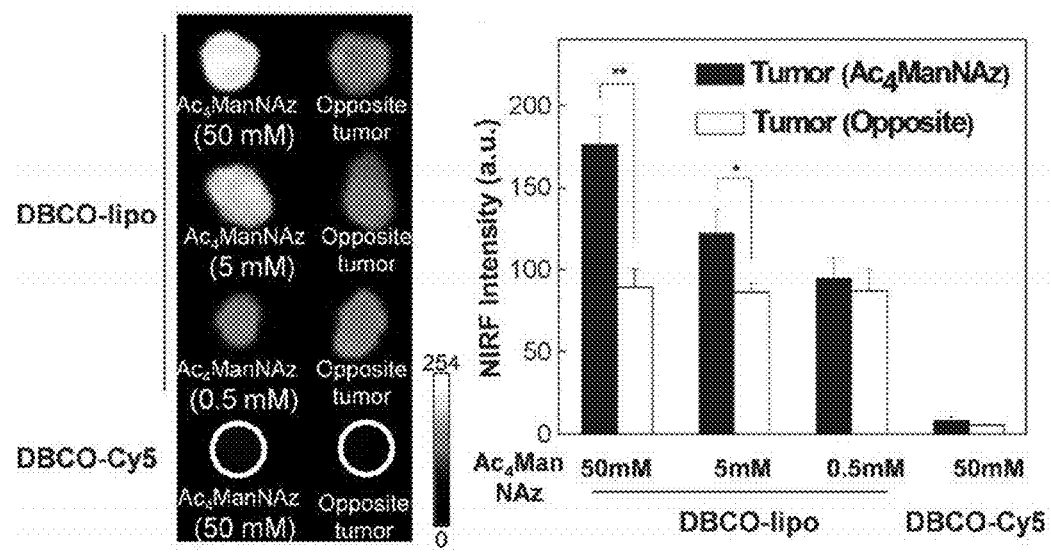
Figure 3D:
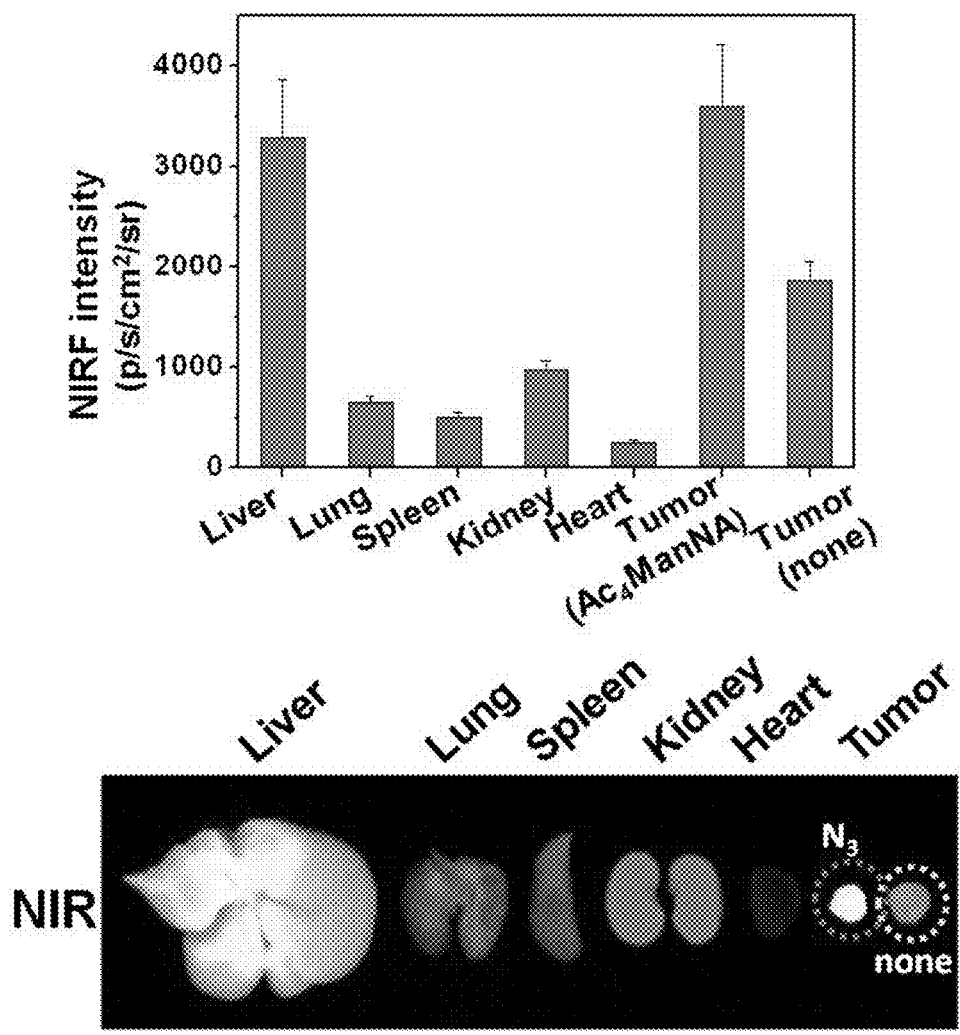

For in vivo studies, xenograft mouse models bearing two tumors in both flanks were prepared by subcutaneous injection of A549 cells. Then, different concentrations of Ac$_4$ManNAz were administered to the left tumors by intratumoral injection for 3 days, while saline was injected to the right tumors as control. After intravenous injection of DBCO-lipo, the biodistribution of DBCO-lipo in the mice was monitored by fluorescence under in vivo and ex vivo conditions. The amount of DBCO-lipo accumulated in the Ac$_4$ManNAz-treated left tumor increased significantly as in the in vitro experiment (see FIG. 3a). From the z-section images of the two tumors, higher fluorescence intensity was observed in the left tumor at all depths, indicating that DBCO-lipo was accumulated in larger amounts over the whole tumor tissue (see FIG. 3b). The fluorescence images obtained from the tumors dissected 5 hours after the injection revealed that the accumulation of DBCO-lipo increased significantly along with the concentration of Ac$_4$ManNAz (see FIG. 3c). In the case of 50 mM Ac$_4$ManNAz-treated tumors, the amount of DBCO-lipo increased almost 2-fold higher than the saline-treated control tumors. This result confirms that the biodistribution of nanoparticles can be artificially controlled in a dose-dependent manner using chemical precursors. The control groups treated with DBCO-free liposomes and the control groups pretreated with TCEP showed no difference in fluorescence intensity of the two tumors. Interestingly, DBCO-SETA-treated mice gave relatively dim images, which may be due its short circulation. This proves that the present disclosure is more suitable for nanoparticles. As seen from FIG. 3d, the fluorescence intensity of DBCO-lipo accumulated in the 50 mM Ac$_4$ManNAz-treated tumors was higher than the fluorescence intensity of DBCO-lipo accumulated in any organ, including liver and kidney.

Figure 4A:
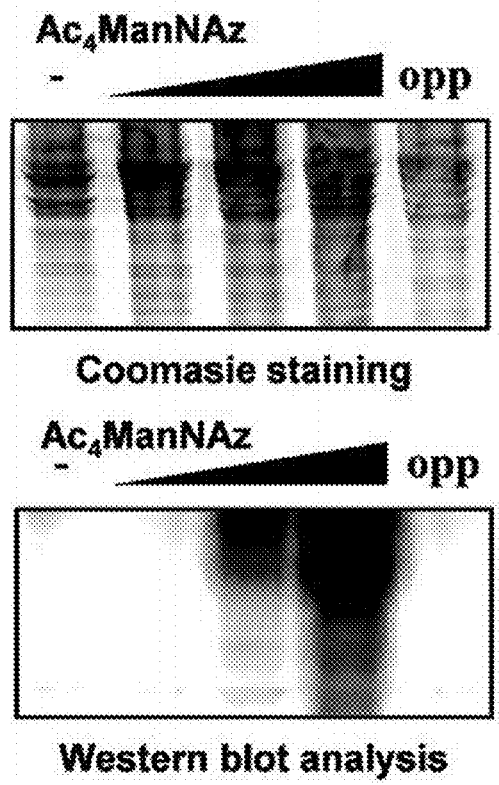
FIGS. 4a-4b show a result of histological analysis of a tumor-bearing mouse model after intravenous injection of DBCO-lipo (FIG. 4a shows a result of Coomassie staining and western blot analysis of Ac$_4$ManNAz-treated tumor tissues, and FIG. 4b shows histological staining and fluorescence images of Ac$_4$ManNAz-treated tumor tissues after intravenous injection of DBCO-lipo).
Figure 4B:
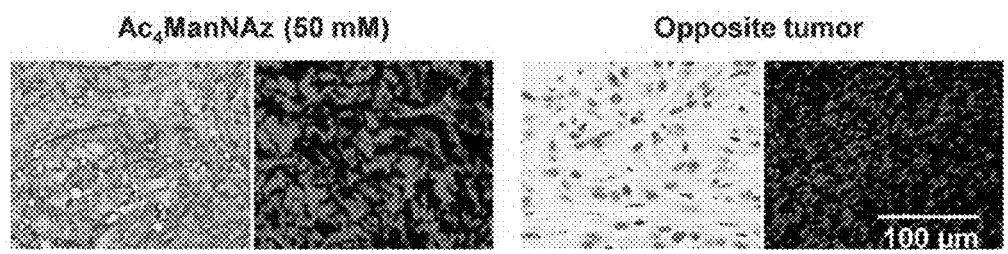
Figure 5:
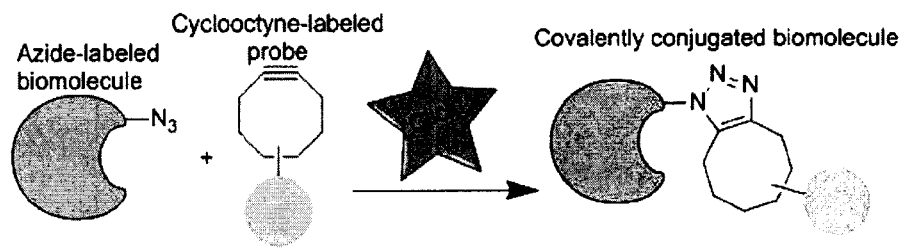
FIG. 5 shows that a bioorthogonal copper-free click chemical reaction requiring no copper catalyst.

The histological analysis of tumors showed that the change in the biodistribution of the nanoparticles is due to the copper-free click chemistry in vivo. The results of Coomassie blue staining and western blot analysis of the tumor tissues also confirmed that the amount of azide groups increased in a dose-dependent manner similarly with the cellular conditions (see FIG. 4a). Histological staining using phosphine-FLAG peptide and FLAG-horse radish peroxidase (HRP) also visualized the increased generation of azide groups in the Ac$_4$ManNAz-treated tumors (see FIG. 4b). The intense red spots of DBCO-lipo in the Ac$_4$ManNAz-treated tumor tissues indicated the correlation between the generated azide groups and the amount of accumulated DBCO-lipo. These results confirm that nanoparticles can be delivered to the target site by in vivo copper-free click chemistry reaction with bioorthogonal chemical groups administered from outside.

In accordance with the present disclosure, accumulation of nanoparticles at a target site in a living system can be increased remarkably and the biodistribution of the nanoparticles can be controlled since the nanoparticles bound to a cell surface are taken up into the cell with time.

While the present disclosure has been described with respect to the specific embodiments, it will be apparent to those skilled in the art that various changes and modifications may be made without departing from the spirit and scope of the disclosure as defined in the following claims.

What is claimed is:

1. A method for in vivo targeting of a nanoparticle, comprising:
    injecting tetraacetylated N-azidoacetyl-D-mannosamine (Ac$_4$ManNAz) at a concentration of at least 50 mM intratumorally to tumors of a living system; and
    intravenously injecting dibenzylcyclooctyne (DBCO)-functionalized liposome into the living system.

2. The method for in vivo targeting of a nanoparticle according to claim 1, wherein the nanoparticle has a size of 10-1000 nm such that in vivo circulation is possible.

3. The method for in vivo targeting of a nanoparticle according to claim 1, wherein the nanoparticle is an organic nanoparticle, an inorganic nanoparticle or an organic-inorganic hybrid nanoparticle.

4. The method for in vivo targeting of a nanoparticle according to claim 3, wherein the organic nanoparticle is selected from the group consisting of liposome, micelle, polymer carrier and protein nanoparticles and the A inorganic nanoparticle is selected from the group consisting of gold and silica nanoparticles.

* * * * *